United States Patent [19]

Ushizawa

[11] Patent Number: 4,889,801

[45] Date of Patent: Dec. 26, 1989

[54] 3α-HYDROXYSTEROID OXIDASE AND QUANTITATIVE ANALYSIS OF 3α-HYDROXYSTEROID MAKING USE OF SAME

[75] Inventor: Koji Ushizawa, Tokyo, Japan

[73] Assignee: Daiichi Pure Chemicals Co., Ltd., Tokyo, Japan

[21] Appl. No.: 63,912

[22] Filed: Jun. 19, 1987

[30] Foreign Application Priority Data

Jul. 8, 1986 [JP] Japan .................. 61-160325

[51] Int. Cl.⁴ .................. C12Q 1/26; C12Q 1/28; C12N 9/08

[52] U.S. Cl. .................. 435/25; 435/28; 435/192

[58] Field of Search .................. 435/25, 28, 192, 810

[56] References Cited

U.S. PATENT DOCUMENTS 4,680,259 7/1987 Cumbo et al. .................. 435/11

4,737,457 4/1988 Evans et al. .................. 435/14

OTHER PUBLICATIONS

Sigma Price List, Feb. 1986, Biochemical and Organic Compounds for Research and Diagnostic Clinical Reagents, p. 625, Item H7127.

*Primary Examiner*—Robert J. Warden
*Assistant Examiner*—Laurie A. Scheiner
*Attorney, Agent, or Firm*—Oblon, Spivak, McClelland, Maier & Neustadt

[57] ABSTRACT

Disclosed herein is a 3α-hydroxysteroid oxidase which oxidizes a 3α-hydroxysteroid into a 3-oxosteroid and hydrogen peroxide. The oxidase may preferably be obtained from a culture broth of *Pseudomonas testosteroni* (ATCC 11996). The oxidase is useful for the quantitative analysis of a 3α-hydroxysteroid. Method and reagent useful for the quantitative analysis of a 3α-hydroxysteroid are also disclosed.

7 Claims, 4 Drawing Sheets

3α-HYDROXYSTEROID OXIDASE AND QUANTITATIVE ANALYSIS OF 3α-HYDROXYSTEROID MAKING USE OF SAME

BACKGROUND OF THE INVENTION

1. Field of the Invention

This invention relates to a 3α-hydroxysteroid oxidase and also to a quantitative analysis of a 3α-hydroxysteroid making use of the 3a-hydroxysteroid oxidase.

2. Description of the Prior Art

Among 3α-hydroxysteroids in an organism, there are steroid hormones such as androsterone, besides bile acid and the like. Of these, bile acid has particularly important significance for clinical diagnoses. Bile acid is composed principally of glucocholic acid, taurocholic acid, glucochenodeoxycholic acid, taurochenodeoxycholic acid, glucodeoxycholic acid, taurodeoxycholic acid and the like. After having been synthesized from cholesterol in a liver, it is circulated through an extremely closed cycle called "enterohepatic circulation system". Bile acid is therefore contained only in a very trace amount in peripheral blood of healthy people. This cycle is however subjected to rhexis by a liver or biliary tract disease, resulting in an increased blood level of bile acid. Making use of such an increase in the blood level of bile acid as an index, it is therefore possible to diagnose such a liver or biliary tract disease and at the same time, to determine its graveness to a certain extent. For these reasons, it has become important to quantitatively analyze bile acid, which is one of 3α-hydroxysteroids, in an organism, especially, serum for the diagnosis of liver and/or biliary tract diseases.

As quantitative analyses of 3α-hydroxysteroids known to date, there are chromatography, enzyme assay, immunoassay, etc. In the field of routine clinical tests, enzyme assay is primarily used owing to its simplicity. Namely, 3α-hydroxysteroid dehydrogenase (hereinafter abbreviated as "3α-HSD") is caused to act on bile acid (a 3α-hydroxysteroid) in the presence of nicotinamide adenine dinucleotide (hereinafter abbreviated as "NAD"), thereby converting AND to reduced nicotinamide adenine dinucleotide (hereinafter abbreviated as "NADH"). Thereafter, its quantitative analysis is carried out by any one of the following methods:

(1) The fluorescence of the resultant NADH is measured.

(2) The resultant NADH is converted back to AND under the action of diaphorase and at the same time, coexisting resazurin is converted to resorufine. The fluorescence of the resorufine is then measured (3) The resultant NADH is converted back to AND under the action of diaphorase and at the same time, coexisting nitroblue tetrazolium is converted to diformazan. The fluorescence of the diformazan is then subjected to colorimetry.

The above methods (1) and (2) are however fluorometric methods, and their procedures are complex and moreover they require expensive equipment. Under the circumstances, they are seldom relied upon in routine tests. On the other hand, the method (3) is poor in sensitivity. Moreover, it requires each sample in a large volume since the blood level of bile acid is extremely low. It is also prone to interference by other components in the sample. The method (3) is not therefore fully satisfactory. Further, the resulting diformazan is a substance having low water solubility and is hence accompanied by drawbacks such that it is adsorbed and is caused to precipitate on instruments employed upon measurement, e.g., cells.

It has therefore been desired to develop an advantageous method for the measurement of a 3α-hydroxysteroid, which is free of drawbacks such as those described above and uses an enzyme.

SUMMARY OF THE INVENTION

The present inventors carried out a research on reaction systems usable for the analyses of 3α-hydroxysteroids. A variety of investigation was also conducted on enzymes usable in such systems. As a result, it has been found that enzymes (hereinafter called "3α-hydroxysteroid oxidase") capable of oxidizing a 3α-hydroxysteroid into its corresponding 3α-oxosteroid and hydrogen peroxide exist in certain microorganisms.

In addition, it has also been found that the 3α-oxosteroid and hydrogen peroxide occur stoichiometrically provided that the 3α-hydroxysteroid oxidase is caused to act on the 3α-hydroxysteroid and oxygen.

The present invention has been completed on the basis of these findings.

In one aspect of this invention, there is thus provided a 3α-hydroxysteroid oxidase, which oxidizes a 3α-hydroxysteroid and forms a 3α-oxosteroid and hydrogen peroxide.

In another aspect of this invention, there is also provided a quantitative analysis of a 3α-hydroxysteroid, which comprises incubating a test sample together with a 3α-hydroxysteroid oxidase or an enzyme preparation containing the 3α-hydroxysteroid oxidase and then measuring the amount of the resultant hydrogen peroxide or 3α-oxosteroid.

In a further aspect of this invention, there is also provided a reagent useful for the quantitative analysis of a 3α-hydroxysteroid, comprising a 3α-hydroxysteroid oxidase and a reagent useful for the measurement of hydrogen peroxide.

In a still further aspect of this invention, there is also provided a reagent useful for the quantitative analysis of a 3α-hydroxysteroid, comprising a 3α-hydroxysteroid oxidase and a reagent useful for the measurement of a 3α-oxosteroid corresponding to the 3α-hydroxysteroid.

The present invention has been completed on the basis of the fact that a 3α-hydroxysteroid can be oxidized stoichiometrically into its corresponding 3α-oxosteroid and hydrogen peroxide and the amount of the 3α-hydroxysteroid can be determined from the hydrogen peroxide or 3α-oxosteroid formed under the action of the enzyme.

The analysis of this invention relies upon the measurement of hydrogen peroxide or the 3α-oxosteroid to be formed under the action of an 3α-hydroxysteroid oxidase. The analysis of this invention therefore does not require operations such as heat treatment of a sample, removal of proteins and extraction, can avoid the adsorption of diformazane on a container unlike the conventional methods, and assures good sensitivity. Further, colorimetry is feasible on the higher frequency side in the measurement system of hydrogen peroxide by making a suitable selection as to the color reagent, leading to a further merit that the influence of interfering substances (hemoglobin, bilirubin, etc.) in serum or plasma can be reduced.

BRIEF DESCRIPTION OF THE DRAWINGS

The above and other objects, features and advantages of the present invention will become apparent from the following description and the appended claims, taken in conjunction with the accompanying drawings, in which:

DETAILED DESCRIPTION OF THE INVENTION AND PREFERRED EMBODIMENTS

Figure 1:
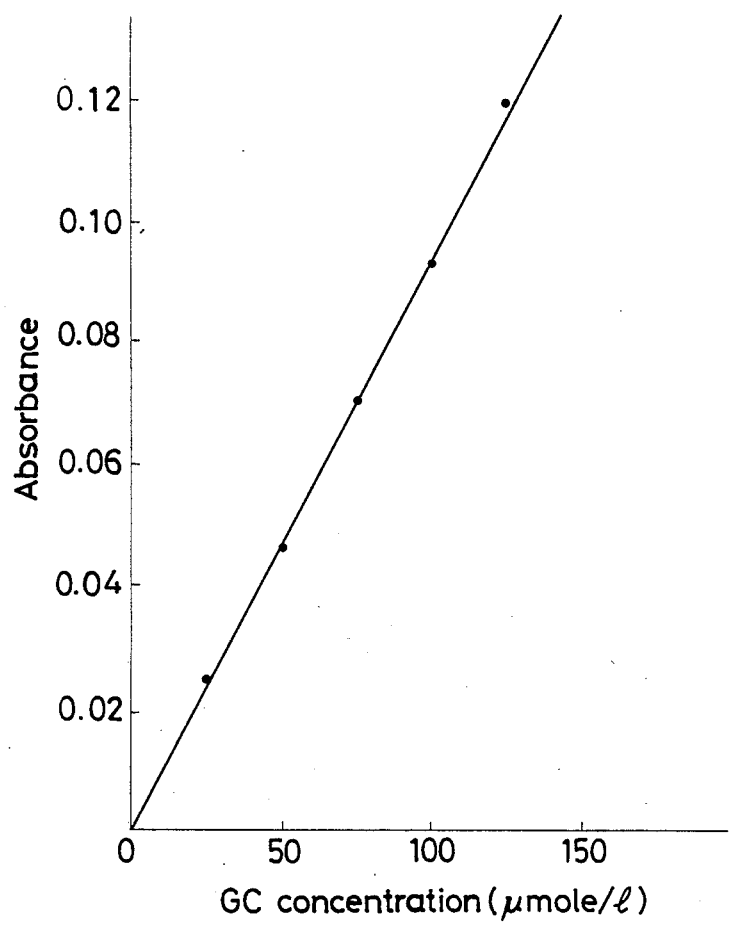
FIG. 1 to FIG. 3 are drawings which show the calibration curves obtained in Examples 3-Example 5 respectively. In each of the drawings, absorbance levels are plotted along the axis of ordinates while GC concentrations are plotted along the axis of abscissas.

Many microorganisms have already been known to metabolize 3α-hydroxysteroids. Especially, those requiring pyridine nucleotide as a coenzyme were found by Talalay, et al. [Nature, 170, 620 (1952)]. A 3α-hydroxysteroid dehydrogenase, which oxidizes a 3α-hydroxysteroid into its corresponding 3α-oxosteroid in the presence of AND as a coenzyme, was subsequently isolated from microorganisms of the genus Pseudomonas. Reference may be had, for example, to Talalay, et al. [Nature, 173, 1189 (1954)], Boyer, J., et al. [Biochemistry, 4, 1825 (1965)], Delin, et al. [Acta., 67, 197 1963)], Marcus, et al. [J. Biol. Chem., 218, 661 (1956)], and Talalay, et al. [J. Biol. Chem., 218, 675 (1956).

The above 3α-hydroxysteroid dehydrogenase has been isolated and produced from various kinds of microorganisms in recent years. For example, it has been reported to have been obtained from strains such as *Pseudomonas putida* NRRL B-11064 [Agric. Biol. Chem. 43, 1521 (1979)], *Bacillus sphaericus* (Japanese Patent Laid-Open No. 157894/1979) and Escherichia freundii [J. Bact., 79, 145 (1960)].

No report has however been issued on the metabolic pathway in which the 3α-hydroxysteroid is oxidized into its corresponding 3α-oxosteroid and hydrogen peroxide.

However, it has now been found for the first time by the present inventors that strains of the genus Pseudomonas and some strains of other genera metabolize 3α-hydroxysteroids into their corresponding 3α-oxosteroids with concurrent production of hydrogen peroxide. The present inventors have hence succeeded to obtain a 3α-hydroxysteroid oxidase from the above strains.

The enzymatic process of the enzyme of this invention can be expressed by the following formula. Enzymes having such effects have not been known. The enzyme of this invention is therefore novel.

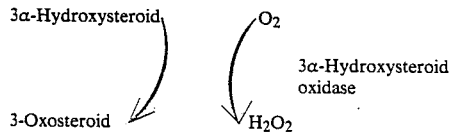

The enzyme of this invention, 3α-hydroxysteroid oxidase, can be obtained by treating in a manner employed routinely upon production of enzymes a microorganism capable of metabolizing a 3α-hydroxysteroid into its corresponding 3α-oxosteroid and hydrogen peroxide out of microorganisms which belong to the genera of *Pseudomonas, Norcardia, Pimerobacter* and the like.

As exemplary microorganisms useful in obtaining the enzyme of this invention, may be mentioned *Pseudomonas testosteroni* ATCC 11996 and that available commercially from SIGMA Corporation as a lyophilized microorganism with a hydroxysteroid dehydrogenase contained therein.

For obtaining the enzyme of this invention from a microorganism, it is only necessary to lyse cell walls with a buffer with a nonionic surfactant contained therein so as to release the enzyme and then to extract the enzyme. These methods are described in detail, for example, in Japanese Patent Publication Nos. 8318/1979 and 28552/1982. Conventionally-known these methods and their modifications can be employed.

More specifically, cells are disrupted by supersonic waves, high-pressure homogenizer, French press, mechanical disruption or the like in the presence of a nonionic surfactant to release the enzyme out of the cells, followed by its solubilization. After removing cell fragments and the like from the resultant solubilized liquid mixture of the 3α-hydroxysteroid oxidase by filtration, centrifugation or the like, nucleic acid which is contained in a relatively large amount is precipitated and removed with protamine sulfate. The thus-obtained crude enzyme solution is purified by suitably using, either singly or in combination, usual purification techniques for enzymes, such as chromatography making use of "Butyl Toyopearl" (trade mark; product of Toyo Soda Mfg. Co., Ltd.), "Sephacryl" (trade mark; Pharmacia AB), "Ion-Exchange Sepharose" (trade name; Pharmacia AB), hydroxyapatite, "ULTROGEL" (LKB Corporation) or the like and salting-out with ammonium sulfate. The resulting purified enzyme is concentrated by ultrafiltration or the like. In order to store the thus-obtained enzyme, it is recommendable to convert it into a solid form, preferably, into a lyophilized form by using a polysaccharide, polyhydric alcohol, amino acid, buffering agent or the like as an excipient.

Typical characteristics of the 3α-hydroxysteroid oxidase of this invention obtained in the manner will be described below with respect to the 3α-hydroxysteroid oxidase originated from *Pseudomonas testosterone* ATCC 11996.

(1) Enzymatic process: Said oxidase oxidizes the 3α-hydroxysteroid specifically at its 3α-hydroxyl group, thereby to form its corresponding 3α-oxosteroid and at the same time to produce hydrogen peroxide.

(2) Substrate specificity: Said oxidase acts on the ethiocholane form (5β-androstan-3α-ol) but not on the androsterone form (5α-androstan-3α-ol).

Figure 4:
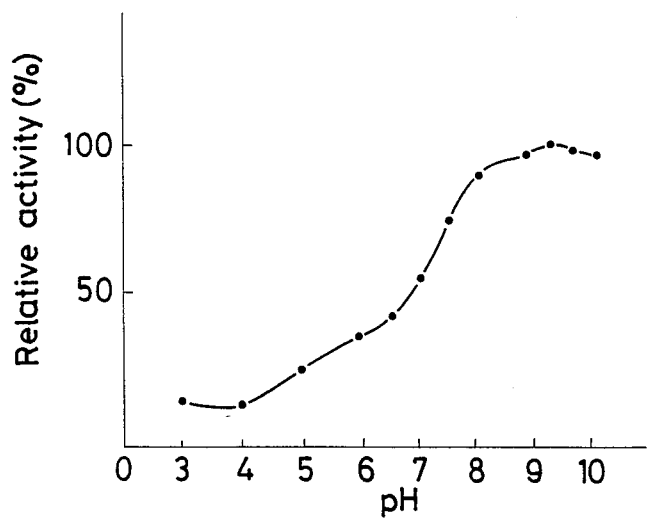
FIGS. 4 and 5 are drawings showing the optimal pH level and pH stability of the enzyme according to this invention. Relative activity levels are plotted along the axis of ordinates, while pH values are plotted along the axis of abscissas.

(3) Optimal pH: The action of said oxidase on ethiocholan-3α-ol-17-one is optimal around pH 9.2 (FIG. 4).

Figure 5:
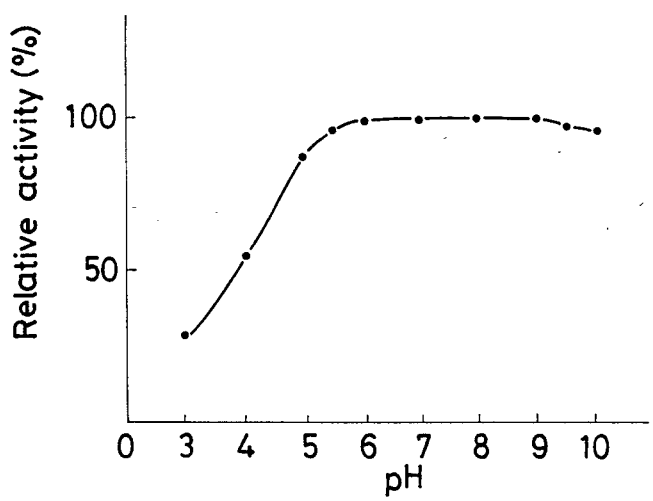

(4) pH stability: When treated at 30° C. for 30 minutes, residual activity of at least 90% was shown at pH 5.5–pH 9.5 (FIG. 5).

(5) Optimal temperature: At pH 7.0, the optimal temperature is near 40° C. in the case of ethiocholan-3α-ol-17-one. (6) Temperature stability: At pH 7.0, at least 95% is stable at 37° C. for 10 minutes.

(7) Km value: $8 \times 10^{-4}$ M (against ethiocholan-3α-ol-17-one).

The quantitative analysis of a 3α-hydroxysteroid, which analysis also pertains to the present invention, may be effected in the following manner, using the 3α-hydroxysteroid oxidase obtained as described above. Namely, a sample containing the 3α-hydroxysteroid is incubated together with the 3α-hydroxysteroid oxidase or an enzyme preparation containing same in the presence of oxygen, so that its corresponding 3α-oxosteroid and hydrogen peroxide are formed. The 3αα-hydroxysteroid is then quantitatively analyzed from the amount of the thus-formed hydrogen peroxide or 3α-oxosteroid. Incidentally, oxygen which is contained in a form dissolved in the reaction mixture under usual conditions is used as the oxygen in the above reaction. It is hence unnecessary to feed oxygen from the outside.

As a method for the quantitative analysis of hydrogen peroxide, it is often practiced to measure the resultant hydrogen peroxide, for example, by a system which contains one or more color reagents capable of undergoing changes in color tone in the presence of hydrogen peroxide. Namely, this is a method to determine the amount of existing hydrogen peroxide by measuring changes in color tone of one or more color reagents in accordance with the colorimetric technique.

As a preferable exemplary method, it may be mentioned to measure the amount of hydrogen peroxide by relying upon a reaction, which takes place between hydrogen peroxide and 4-aminoantipyrine in the presence of an excess amount of phenol and a peroxidase, and then to determine the amount of the 3α-hydroxysteroid from the amount of the hydrogen peroxide. The amount of the resultant hydrogen peroxide may also be measured by other suitable reaction reagent systems, for example, a combination of a peroxidase, 4-aminoantipyrine, and a phenol, naphthol or aniline compound; a combination of a peroxidase, 3-benzothiazolinonehydrazone (MBTH) and an aniline compound; a combination of a peroxidase and 2,2'-amidinobis(3-ethylbenzothiazoline-6-sulfonic acid (ABTS); and a combination of a peroxidase and a leuco methylene blue derivative. From the thus-measured amount of the resultant hydrogen peroxide, the amount of the 3α-hydroxysteroid can be determined.

On the other hand, the amount of the 3-oxosteroid may be measured, for example, in the following manner. After extracting the 3-oxosteroid from the reaction mixture with a suitable organic solvent (ethyl acetate, ethyl ether or the like) and concentrating the extract, the resultant concentrate is developed by a matching developer (e.g., a benzene-chloroform-methanol system or an ethyl acetate-benzene system), a mobile spot is confirmed and isolated by a chemical analysis method such as UV absorption or iodine spraying and is then quantitatively analyzed by a method known per se in the art. Another method may also be used as an alternative, in which the resultant 3-oxosteroid is fed to and measured with a redox colorimetric system by making use of the fact that the 3-oxosteroid is oxidized and its associated electron receptor is reduced concurrently when a 3-oxosteroid-$\Delta^4$-dehydrogenase (E.C. 1. 3. 99.6) is caused to act on the 3-oxosteroid (Japanese Patent Application No. 64547/1985). As redox color reagents useful in the practice of the latter method, may be mentioned nitro blue tetrazolium, indonitrotetrazolium, 3-(4,5-dimethyl-2-thiazolyl)-2,5-diphenyl-2H-tetrazolium bromide (MTT), 1,1'-(3,3'-dimethoxy-4,4'-biphenylene)bis{5-(4-nitrophenyl)-3-[4-(2-hydroxy-3-2-hydroxyethyldiethylaminopropoxy)phenyl]}-2H-tetrazolium chloride (MTB), etc.

These quantitative analyses of a 3α-hydroxysteroid may each be carried out in an automatic fashion, in which the quantitative analyses of many samples are conducted continuously, or in a non-automatic fashion in which the quantitative analyses of a small number of samples are conducted individually.

For the quantitative analysis of a 3α-hydroxysteroid, it is convenient to use quantitative analysis reagents of the following forms:

(1) a reagent useful for the quantitative analysis of the 3α-hydroxysteroid, which contains a 3α-hydroxysteroid oxidase and a reagent useful for the measurement of hydrogen peroxide; and (2) a reagent useful for the quantitative analysis of the 3α-hydroxysteroid, which contains a 3α-hydroxysteroid oxidase and a reagent useful for the measurement of its corresponding 3-oxosteroid.

As exemplary reagents useful for the measurement of hydrogen peroxide, may be mentioned a combination of a peroxidase, 4-aminoantipyrine and phenol as well as the above-described various reagents. As the reagent useful for the measurement of the 3-oxosteroid on the other hand, the above-described 3-oxosteroid-$\Delta^4$-dehydrogenase or a redox reagent may be mentioned by way of example.

The reagent of this invention useful for the quantitative analysis of a 3α-hydroxysteroid may preferably contain a 3α-hydroxysteroid oxidase at a final concentration of 100–1,000 units/ml. Incidentally, 1 unit of the 3α-hydroxysteroid oxidase means an enzymatic quantity that can produce 1 mole of hydrogen peroxide per minute at pH 9.0 and 37° C.

These quantitative analysis reagents may each be formulated into a preparation with all necessary components incorporated therein. Alternatively, it may also be possible to formulate the enzymes of the 3α-hydroxysteroid oxidase and peroxidase or the 3α-hydroxysteroid oxidase and 3-oxosteroid-$\Delta^4$-dehydrogenase and the remaining reagents into separate preparations. Especially, it is preferable to form the enzymes into a lyophilized powder or concentrated liquid form so that a user can dilute and use same upon measurement.

Having generally described the invention, a more complete understanding can be obtained by reference to certain specific examples, which are provided herein for purposes of illustration only and are not intended to be limiting unless otherwise specified.

EXAMPLES

The present invention will hereinafter be described specifically by the following Examples.

EXAMPLE 1

Preparation of 3α-Hydroxysteroid Oxidase

To 20 l of a growth medium which had been sterilized in advance, 500 ml; of a seed culture broth of *Pseudomonas testosterone* ATCC 11996 was inoculated. The pH of the growth medium was 7.00 and its principal components were as follows:

| Yeast extract | 10 (g/l) |
|---|---|
| $(NH_4)_2HPO_4$ | 1 |
| $(NH_4)H_2PO_4$ | 1 |
| $KH_2PO_4$ | 2 |
| $MgSO_4.7H_2O$ | 0.2 |

| -continued | |
|---|---|
| Yeast extract | 10 (g/l) |
| NaCl | 0.01 |
| ZnSO$_4$.7H$_2$O | 0.005 |
| MnSO$_4$.3H$_2$O | 0.005 |
| CuSO$_4$.5H$_2$O | 0.0005 |
| Sodium lactate | 0.5% final concentration |

After the culture medium was incubated at 28° C. for 24 hours to allow the microorganism to grow, an acetone solution of testosterone was added to a final concentration of 50–500 mg/l in the medium so that the production of a 3α-hydroxysteroid oxidase was induced. Thereafter, the microorganism was cultured at the same temperature for 10–24 hours. After completion of the culture, the resultant culture broth was centrifuged to separate and collect cells. The thus-collected cells were suspended at 5° C. in 5 volumes of a 0.02 M phosphate buffer of pH 7.0, which contained 1% (w/v) of "Triton X-100" (BDH Ltd.), to a total volume of 1 l. By a cell disrupter, DINO-MILL (trade mark; manufactured by Willy A. Bachofen Maschinenfabrik AG), the cells were disrupted to release the enzyme. The resultant mixture was centrifuged and an extract containing the 3α-hydroxysteroid oxidase was obtained from the supernatant. The extract was then added with 430 g of ammonium sulfate to a final concentration of 65% saturation, the precipitated fraction was collected by centrifugation. The precipitate was dissolved in a 0.1M phosphate buffer (pH 7) containing 0.1% of "Triton X-100" and the resultant mixture was dialyzed for 24 hours against the same buffer in order to remove any remaining ammonium sulfate. The dialyzate was then caused to pass through a column (capacity: 200 ml) packed with "DEAE-Sepharose CL-6B" (trade name; product of Pharmacia AB) which had beforehand been equilibrated with the same buffer (pH 7.0) containing 0.1% of "Triton X-100". The intended 3αα-hydroxysteroid oxidase was eluted with the same buffer containing 0.1% of "Triton X-100" in accordance with the linear gradient technique in which the molar concentration of sodium chloride was gradually increased. Eluate fractions, which contained the 3α-hydroxysteroid oxidase, were concentrated at 5° C. through an ultrafiltration membrane. The concentrated enzyme solution (20 ml) had activity, for which a 3α-hydroxysteroid was oxidized at 37° C. The total recovery rate was 10%, while the specific activity was 0.5 unit/mg.

An azide was added as a preservative to the enzyme solution. The resultant solution could be stored for 2–3 months at 5° C. During the storage period, the activity was retained fully. Relative activities of the thus-obtained 3α-hydroxysteroid oxidase for various substrates are summarized in Table 1.

TABLE 1

| Substrate | R.A.*(%) |
|---|---|
| Ethiocholan-3α-ol-17-one (5β-androstane) | 140 |
| 5α-Androstan-3α-ol-17-one (androsterone) | 0 |
| 5β-Androstan-3,17-dione | 18 |
| 5α-Androstan-3,17-dione | 0 |
| Testosterone | 0 |
| Cholic acid | 100 |
| Cithocholic acid | 57 |
| Deoxycholic acid | 86 |
| Chenodeoxycholic acid | 89 |
| Glycocholic acid | 95 |

TABLE 1-continued

| Substrate | R.A.*(%) |
|---|---|
| Cholesterol | 0 |

*R.A. (relative activity) is indicated with the R.A. cholic acid being 100.

EXAMPLE 2

Quantitative Analysis of Ethiocholane-3α-ol-17-one

Prepared first of all was a measuring reagent formed of a 0.1M phosphate buffer (pH 7) which contained 20 units/l of the 3α-hydroxysteroid oxidase (with 1% of "Triton X-100" contained therein), 60 mmoles of 4-aminoantipyrine, 30 mmoles of phenol and 10,000 units/ml of a peroxidase.

To 0.5 ml of the above measuring reagent, 200 μl of a methanol solution of ethiocholan-3α-ol-17-one was added, followed by a reaction at 37° C. for 10 minutes. The absorbance was then measured at a wavelength of 500 nm. With a measuring reagent similar to that used in the above procedure except for the omission of the 3α-hydroxysteroid oxidase, a similar operation was also conducted with respect to the same sample. Results were used as a sample blank. As test samples, were used those obtained by diluting ethiocholan-3αa-ol-17-one into various concentrations. Results are shown in Table 2.

TABLE 2

| Ethiocholan-3α-ol-17-one (μmole/l) | 10 | 20 | 40 | 60 | 80 |
|---|---|---|---|---|---|
| Absorbance | 0.012 | 0.023 | 0.047 | 0.072 | 0.095 |

Example 3

Quantitative Analysis of Bile Acid in Serum

After adding 200 μl of serum or a standard solution to 0.5 ml of the same measuring reagent as that used in Example 2 and reacting them at 37° C. for 10 minutes, a measurement was conducted at 500 nm. With a measuring reagent similar to that used in the above procedure except for the omission of the 3α-hydroxysteroid oxidase, a similar operation was also conducted with respect to the same sample. Results were used as a sample blank. As test samples, were used those obtained by diluting into various concentrations serum which had been added with glycocholic acid (hereinafter abbreviated as "GC") in advance. Results are shown in Table 3. In addition, a calibration curve prepared on the basis of the results is shown in FIG. 1.

TABLE 3

| GC concentration (μmole/l) | 25 | 50 | 75 | 100 | 125 |
|---|---|---|---|---|---|
| Absorbance | 0.024 | 0.046 | 0.070 | 0.093 | 0.119 |

Example 4

Figure 2:
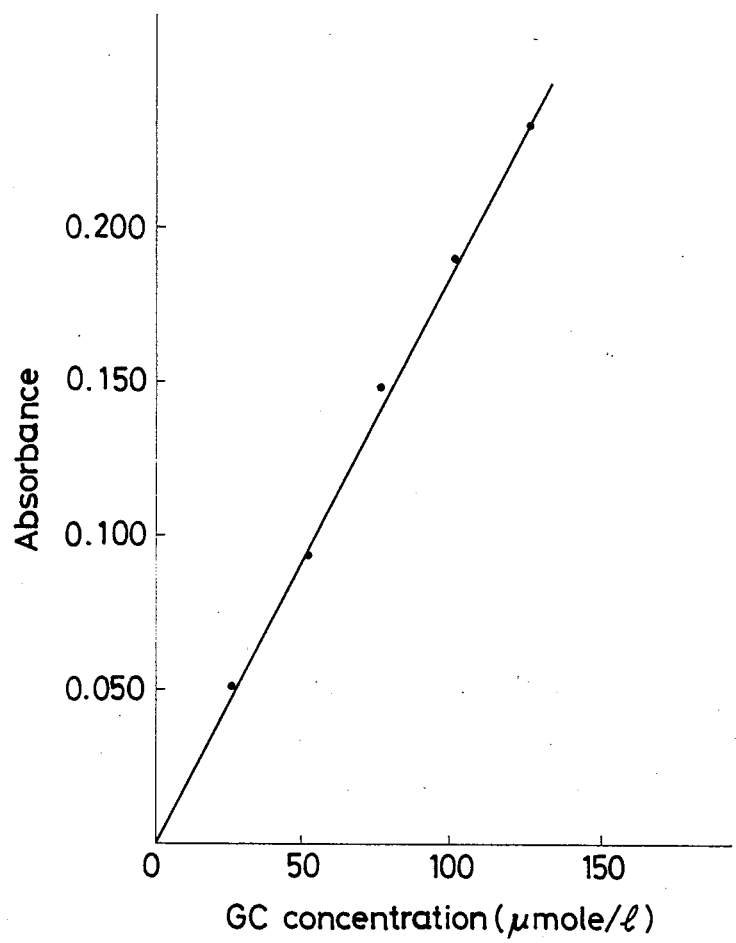

Using the same measuring reagent as that employed in Example 2 except for the use of 30 mM of sodium N-ethyl-N-(2-hydroxy-3α-sulfopropyl)-3,5-dimethoxyaniline place of phenol, a calibration curve was determined by the same method as the measuring method of Example 3 except that the measuring wavelength was changed to 600 nm. Results are shown in Table 4. The calibration curve prepared on the basis of the results is shown in FIG. 2.

TABLE 4

| GC concentration (μmole/l) | 25 | 50 | 75 | 100 | 125 |
|---|---|---|---|---|---|
| Absorbance | 0.050 | 0.094 | 0.148 | 0.191 | 0.243 |

EXAMPLE 5

Figure 3:
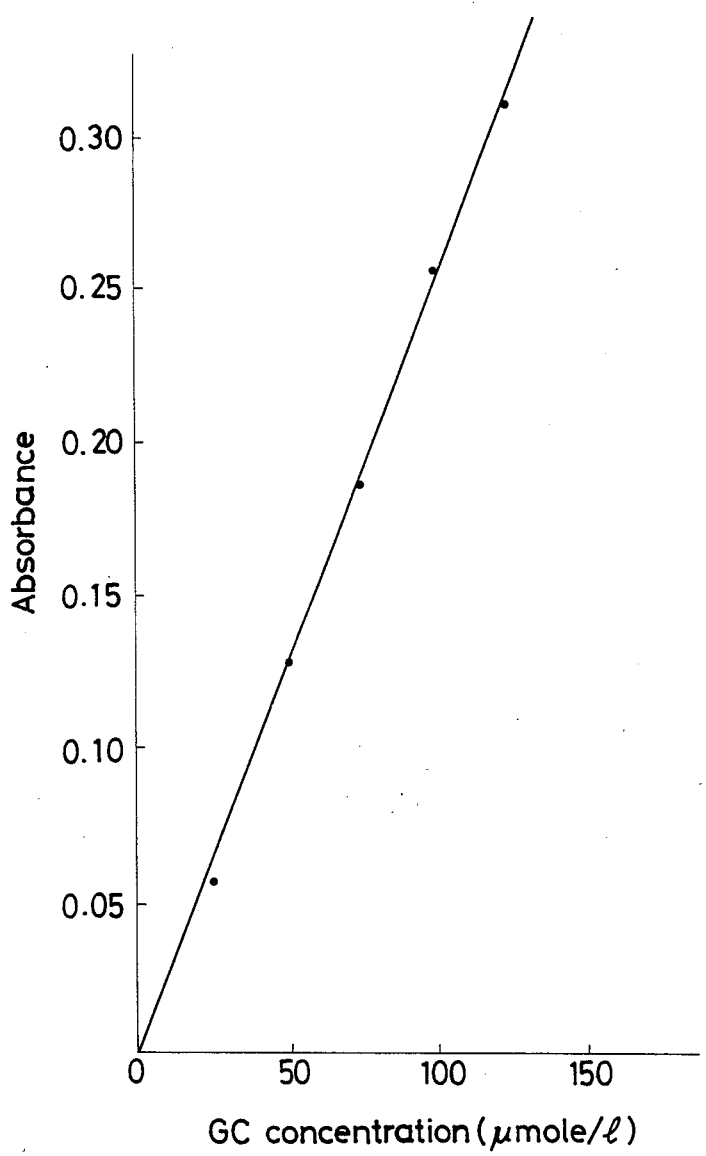

A calibration curve was determined by the same method as the measuring method of Example 3 except that 10 mmole/l of leuco methylene blue was used instead of DAOS of Example 4, the amount of serum or a test sample was 50 μm, and the measuring wavelength was 670 nm. Results are summarized in Table 5. Further, the calibration curve prepared on the basis of the results are shown in FIG. 3.

TABLE 5

| GC concentration (μmole/l) | 25 | 50 | 75 | 100 | 125 |
|---|---|---|---|---|---|
| Absorbance | 0.056 | 0.126 | 0.185 | 0.255 | 0.311 |

EXAMPLE 60

Separately using ten serum samples in an amount of 100μl each, operations similar to that of Example 4 were conducted to determine the absorbance levels of the respective serum samples. From their calibration curves, the amounts of the 3α-hydroxysteroid in the respective serum samples were calculated. Further, the same samples were also measured by "ENZABILE" (trade mark; product of Nygard Company and Daiichi Pure Chemicals Co., Ltd.), which was a kit for measuring the 3α-hydroxysteroid with a 3α-hydroxysteroid dehydrogenase. In Table 6, results are given together with the above calculation results.

TABLE 6

| | Amount of the 3α-hydroxysteroid (μmole/l) | |
|---|---|---|
| Sample No. | Method of Ex. 4 (sample: 100 μl) | "ENZABILE" kit (sample: 200 μl) |
| 1 | 15.6 | 15.3 |
| 2 | 7.6 | 6.7 |
| 3 | 75.8 | 75.8 |
| 4 | 16.2 | 15.9 |
| 5 | 21.3 | 19.1 |
| 6 | 42.0 | 38.2 |
| 7 | 43.3 | 39.5 |
| 8 | 11.8 | 10.2 |
| 9 | 8.2 | 8.9 |
| 10 | 108.3 | 101.9 |

EXAMPLE 7

A measuring reagent was prepared by using 5 mmoles of NTB and 100 units of 3-oxo-5β-steroidΔ$^4$-dehydrogenase instead of the 4-aminoantipyrine, phenol and peroxidase of Example 2.

A calibration curve was determined by the same method as the measuring method of Example 2 except that the measuring wavelength was changed to 540 nm. Results are shown in Table 7.

TABLE 7

| Ethiocholan-3α-ol-17-one (μmole/l) | 10 | 20 | 40 | 60 | 80 |
|---|---|---|---|---|---|
| Absorbance | 0.017 | 0.032 | 0.066 | 0.101 | 0.133 |

Having now fully described the invention, it will be apparent to one of ordinary skill in the art that many changes and modifications can be made thereto without departing from the spirit or scope of the invention as set forth herein.

I claim:

1. A 3α-hydroxysteroid oxidase, which oxidizes a 3α-hydroxysteroid and forms a 3-oxosteroid and hydrogen peroxide.

2. The 3α-hydroxysteroid oxidase having been obtained by culturing a culture broth of *Psuedomonas testosterone* (ATCC 11996).

3. A quantitative analysis of a 3α-hydroxysteroid, which comprises incubating a test sample together with a 3α-hydroxysteroid oxidase or an enzyme preparation containing the 3α-hydroxysteroid oxidase and then measuring the amount of the resultant hydrogen peroxide or 3-oxosteroid as an indication of the amount of 3α-hydroxysteroid.

4. A reagent useful for the quantitative analysis of a 3α-hydroxysteroid, comprising a 3α-hydroxysteroid oxidase and a reagent useful for the measurement of hydrogen peroxide.

5. The reagent as claimed in claim 4, wherein the reagent for the measurement of hydrogen peroxide is selected from a combination of a peroxidase, 4-aminoantipyrine, and a phenol, naphthol or aniline compound; a combination of a peroxidase, 3-benzothiazolinonehydrazone and an aniline compound; a combination of a peroxidase and 2,2'-amidinobis(3-ethylbenzothiazoline-6-sulfonic acid; and a combination of a peroxidase and a leuco methylene blue derivative.

6. A reagent useful for the quantitative analysis of a 3α-hydroxysteroid, comprising a 3α-hydroxysteroid oxidase and a reagent useful for the measurement of a 3-oxosteroid corresponding to the 3α-hydroxysteroid.

7. The reagent as claimed in claim 6, wherein the reagent useful for the measurement of the 3α-oxosteroid comprises a combination of a 3-oxosteroid-Δ$^4$-dehydrogenase and a redox color reagent.

* * * * *